United States Patent [19]

Wurtman et al.

[11] 4,309,445
[45] Jan. 5, 1982

[54] D-FENFLURAMINE FOR MODIFYING FEEDING BEHAVIOR

[75] Inventors: Richard J. Wurtman; Judith J. Wurtman, both of Boston, Mass.

[73] Assignee: Massachusetts Institute of Technology, Cambridge, Mass.

[21] Appl. No.: 159,549

[22] Filed: Jun. 16, 1980

[51] Int. Cl.³ .............................................. A61K 31/13
[52] U.S. Cl. .................................................. 424/325
[58] Field of Search ......................................... 424/325

[56] References Cited

U.S. PATENT DOCUMENTS 3,198,834  8/1965  Beregi et al. ..................... 260/570.8

OTHER PUBLICATIONS

Merck Index, 9th Ed. 1976, Entry No. 3902.
Wurtman et al., Science, vol. 198, pp. 1178–1180, 12/77.
Current Medical Research & Opinion, vol. 6, Suppl. 1, pp. 28–33, 1979.
Life Sciences, vol. 24, pp. 894–904, 1979.
Unger et al., Ann. Rev. Physiol., (1978), 40, p. 315.

*Primary Examiner*—Frank Cacciapaglia, Jr.
*Attorney, Agent, or Firm*—Arthur A. Smith, Jr.; Paul J. Cook

[57]     ABSTRACT

Compositions containing controlled amounts of d-fenfluramine are administered to block the intermittent carbohydrate cravings without necessarily suppressing other food intakes.

2 Claims, No Drawings

D-FENFLURAMINE FOR MODIFYING FEEDING BEHAVIOR

BACKGROUND OF THE INVENTION

This invention concerns a new method of treating the syndrome of carbohydrate craving during which patients present an abnormal appetite for carbohydrate at definite hours.

At the present time, patients having a strong appetite for carbohydrate were not treated before appearance of obesity. At that stage, the use of compositions of large amounts of bulky substances or appetite-suppressant drugs have been utilized. The suppression of appetite was seen to result from a propensity to eat slower, to wait longer between meals, or to stop eating sooner. Such drugs show no selectivity on the kind of feeding and have unwanted side effects such as induction of hyperactivity.

A preferred method of treatment would involve the correction of the very nature of the feeding habits of some patients having an immoderate appetite for certain kinds of carbohydrate-containing food, particularly between meals. Such a state does not always entail obesity, but can indicate some metabolic disturbances or some neurotic troubles due to anxiety of becoming overweight.

Prior to the present invention, it has been known to administer dextro, levo-fenfluramine or fluoxetine to an animal (rat) in order to selectively reduce consumption of carbohydrates while not significantly reducing consumption of protein. These results are shown by Wurtman et al, *Science,* vol. 198, pp. 1178–1180, December, 1977; *Current Medical Research and Opinion,* vol. 6, Suppl. 1, pp. 28–33, 1979 and *Life Sciences,* vol. 24, pp. 894–904, 1979.

The d-isomer of fenfluramine and the salts thereof are known products which have been disclosed in the U.S. Pat. No. 3,198,834. In the same patent, the d-isomers at doses from about 5 mg to 50 mg per kg, have been generically disclosed as having an anorectic and a lipolytic activity in rates approximately three times greater than that of the corresponding l-isomer. The corresponding racemic mixture has an intermediate activity.

SUMMARY OF THE INVENTION

The present invention provides an appropriate treatment for carbohydrate cravings, i.e., for the patient presenting an abnormal appetite for carbohydrates at definite hours of the day or night. The invention is based on the discovery that the d-isomer of fenfluramine selectively eliminates this abnormal and intermittent appetite for carbohydrates while maintaining a normal protein and lipid intake. The effect of d-fenfluramine concerns all sweet foods and those which produce glucose during the gastrointestinal transit, and that such inhibition does not function simply through a control of the caloric intake.

DESCRIPTION OF SPECIFIC EMBODIMENTS

The present invention relates to novel pharmaceutical compositions for treating the syndrome of carbohydrate craving during which the patients present an abnormal appetite at definite hours of the day or night. Specifically, the invention provides pharmaceutical compositions having as an active ingredient the d-isomer of fenfluramine or 1-meta-trifluoro-methylphenyl-2-ethyl-aminopropane or a salt thereof mixed with an inert non-toxic pharmaceutical carrier.

Suitable additional salts can be formed from the following acids; the hydrohalic acid, sulfuric acid, phosphoric acid or an organic acid such as acetic acid, valeric acid, caproic acid, benzoic or nicotinic acid.

The inert non-toxic pharmaceutical excipient of choice utilized depends on the mode of administration. The compositions of this invention are suitable for parenteral, buccal, sublingual or rectal administration. The resulting pharmaceutical compositions are, for example, tablets, coated tablets, capsules, soft gelatine capsules, drinkable emulsions, suspensions or solutions for oral or injectable administration, sublingual tablets or suppositories. They may also be formulated into a sustained release form. Among the various excipients which may be used for these purposes include talc, magnesium stearate, calcium carbonate, sodium or magnesium phosphate, lactose or silica or the like. To the solid forms may be added a filler, a diluent, a binder such as ethyl-cellulose, dihydroxypropyl cellulose, carboxymethylcellulose, arabic gum, tragacanth gum or gelatine. The compositions of this invention may also be flavored, colored or coated with a wax or a plasticizer.

It has now been found that the d-isomer of fenfluramine is endowed with interesting and very specific properties which put it and its salts in a specific class among a broad disclosure of closely related compounds. This invention is based upon the discovery that the compositions of low doses of d-fenfluramine selectively suppress cravings for carbohydrates without disturbing the normal food intake.

We have found that such a special activity of the d-isomer which has never been suggested, is particularly useful for the treatment of patients having at definite hours of day or night a strong carbohydrate craving, that is an abnormal behavior of eating carbohydrate out of hunger.

Such patients are characterized by:
- a great appetite for carbohydrate foods which are often the same,
- an appetite often arising without anxiety,
- an appetite occurring according to a regular circadian cycle, and the resulting circadian maxima can be in relation to the menstruation cycle,
- often not overweight at the onset of the illness,
- sometimes associated with a so-called prediabetic state.

These patients need at definite hours, between meals, a high level of carbohydrate consumption in the form of snacks: doughnuts, fried potatoes, potato chips, pretzels, ice cream, whole meal or chocolate cookies, etc. Such a syndrome may be linked to signs of diabetus mellitus in persons at risk.

For these patients, the administration of a composition containing between about 5 to 200 mg of d-fenfluramine, depending upon the body weight of the patient, decreases the abnormal craving for carbohydrate foods at definite hours of the circadian cycle, and this result is not inhibited by the intake of a meal in which no visible alteration in the selection of basic nutrients has been observed. In accordance with this invention, d-fenfluramine is administered in an amount of between about 5 and 100 mg/day, preferably about 10 and 60 mg/day. At dosages above and below these amounts, the selective decrease of carbohydrate consumption does not occur to a significant degree.

The surprising and novel activity of the compositions of low doses of d-fenfluramine cannot be explained by the existing data on biological pharmacology of anorectic drugs which, at high doses, appear to depend on a different mechanism of action. The d-isomer of fenfluramine at usual or high dosage is more potent in inhibiting global food intake (protein and lipid as well as carbohydrate) than the l-isomer. This activity appears to be mediated by the serotoninergic system, since:

1. The neurochemical effects of those drugs on serotonin level in the brain are significantly modified and can explain how the global food intake is inhibited.

2. Other data show that lesions of the serotoninergic terminals in specific brain areas block the effect of high doses of dl-fenfluramine on global food intake.

3. The sedative action of these doses of dl-fenfluramine has also been considered as a consequence of serotoninergic mechanisms.

The new properties of compositions of low doses of d-fenfluramine which inhibit carbohydrate cravings, appear to depend on a different mechanism in relation to the central control of regulation of the energy balance: our observations show that its action is very similar to the action of somatostatin; a peptide localized in the hypothalamus, in the digestive endothelium and in the pancreatic islets. When injected into the 3rd ventricle of the rat, at very low doses, it decreases food intake and has a general behavioral effect of inhibition of the desire for carbohydrates, and inhibits absorption of carbohydrates. (Unger et al, Ann. Rev. Physiol, 1978, 40, p. 315).

While applicants do not intend to be bound by a theory of the mechanism of this invention, the following examples are merely intended to illustrate the invention and are not intended to limit the same.

EXAMPLE I

Selectivity in the Selection of Basic Nutrients at Low Doses

Material and Methods

Fifty-three male rats 21 to 48 days old (Charles River Breeding Laboratories, Wilmington, MA.) were housed singly in suspended cages and allowed free access to water. Room temperature was kept at 22° C. The animals were trained to consume all of their daily food during an 8-hour dark period and to select their food from two pans containing different diets which were isocaloric and contained 5 or 45 percent protein. The rats were injected with either d-fenfluramine (1.25 or 2.5 mg/kg), racemic fenfluramine (2.5 mg/kg) or saline at the beginning of the dark period and were given access to the food pans immediately afterwards. The pans were weighed before presentation and at intervals during the eight-hour feeding period. The number of grams of protein that each animal had consumed and the proportion of total caloric intake represented by this protein were calculated for each interval.

Results

TABLE I

EFFECT OF D-, AND DL-FENFLURAMINE UPON FOOD INTAKE AND PROTEIN CONSUMPTION

| Number of Rats | Treatment | DIET 45% Protein | 5% Protein | Total Food | Total Protein | % Protein |
|---|---|---|---|---|---|---|
| 15 | saline | 5.2 | 3.1 | 8.4 | 2.5 | 29.7 |
| 12 | 1.25 mg/kg of d-fenflu. | 4.5 | 1.0 | 5.5 | 2.1 | 37.8 |
| 7 | 2.5 mg/kg of d-fenflu. | 2.8 | 2.0 | 4.8 | 1.36 | 28.3 |
| 19 | 2.5 mg/kg of dl-fenflu. | 4.6 | 0.97 | 5.54 | 2.1 | 37.9 |

The superiority of d-fenfluramine is clearly shown because:

1. Both d- and dl-drugs reduced the total food intake, but the same result was obtained with half the dose of d-isomer.

2. At 1.25 mg of d-fenfluramine per kilo, rats reduced food intake but increased the proportion of protein from 29.7 to 37.8%, suggesting that a normal quantity of proteinic food was consumed, and that the quantity of carbohydrate was strongly decreased.

3. At 2.50 mg of d-fenfluramine per kilo, the selective anti-carbohydrate effect did not appear any more: this very particular figure of "inversion" of results with increasing doses is most familiar to physiologists and strongly suggests that a very specific system of regulation is concerned. It relates to a counter regulation mechanism overcoming the first at higher doses of the same drug. The whole history of research on autonomic nervous system drugs gives examples of such "diphasic" action, for very specific inhibitors.

4. The same specificity in protein intake was obtained with 2.50 mg/kg of the racemic mixture as well as with 1.25 mg/kg of the d-isomer, indicating that this effect was due only to d-fenfluramine, and that levo-fenfluramine has no significant effect. Accordingly, we found that higher doses of racemic mixtures (5 mg/kg) also had no selective effect on glucose food intake.

EXAMPLE II

Suppression of Consumption of Protein-Poor Diet by D-Fenfluramine

Materials & Methods

One hundred and twenty male rats, 21–48 days old, as above, received saline, dextro-levo fenfluramine (2.5 mg/kg), d-fenfluramine (1.25 or 2.5 mg/kg), or levo-fenfluramine (2.5 mg/kg) intraperitoneally, and were given access to food pans containing 5% or 45% protein (isocaloric; iso-carbohydrate) immediately thereafter. Data describe the grams of the protein-poor diet (5%) consumed during the subsequent one hour period.

Results

TABLE II

| Treatment | Number of Rats | 5% Protein Diet Consumed (Grams) |
|---|---|---|
| saline | 46 | 3.48 |
| dextro-levo fenfluramine (2.5) | 41 | 1.01 |
| d-fenfluramine (2.5) | 10 | 1.54 |
| d-fenfluramine (1.25) | 12 | 0.30 |
| levo fenfluramine (2.5) | 11 | 3.70 |

As in Example I, d-fenfluramine administration caused a major decrease in the quantity of carbohydrate-rich, protein-poor food that the rats chose to consume. Half the d-l fenfluramine dose of 2.5 mg/kg was sufficient to cause an even-more-major reduction in consumption of this diet, after d-fenfluramine; in contrast, 2.5 mg/kg of l-fenfluramine had no effect.

We claim:

1. A method for treating human patients having the syndrome of abnormal carbohydrate craving between meals which consists of administering to said patient a unit dosage form of a composition which comprises between about 5 mg and 100 mg per day of an active composition comprising the dextro optically active isomer of 1-(meta-trifluoromethylphenyl)-2-ethylaminopropane or a physiologically acceptable salt thereof in admixture with an inert non-toxic carrier.

2. A method of claim 1 wherein the dosage of the active isomer ranges from 10 to 60 mg per day.

* * * * *

UNITED STATES PATENT AND TRADEMARK OFFICE

CERTIFICATE EXTENDING PATENT TERM
UNDER 35 U.S.C. § 156

PATENT NO.      :   4,309,445

ISSUED          :   January 5, 1982

INVENTOR(S)     :   Richard J. Wurtman et al.

PATENT OWNER    :   Massachusetts Institute of Technology

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 1,343 days from June 16, 2000, the original expiration date of the patent, with all rights pertaining thereto as provided by 35 U.S.C. § 156(b).

I have caused the seal of the Patent and Trademark Office to be affixed this 2nd day of September 1998.

Bruce A. Lehman
Assistant Secretary of Commerce and
Commissioner of Patents and Trademarks